United States Patent
Tokumaru et al.

(10) Patent No.: US 10,593,488 B2
(45) Date of Patent: Mar. 17, 2020

(54) NONAQUEOUS ELECTROLYTIC SOLUTION FOR ELECTRIC DOUBLE LAYER CAPACITORS

(71) Applicant: OTSUKA CHEMICAL CO., LTD., Osaka (JP)

(72) Inventors: Yoshihisa Tokumaru, Tokushima (JP); Yoshihiro Okada, Tokushima (JP); Taiji Nakagawa, Tokushima (JP); Shoji Hiketa, Tokushima (JP); Koichi Sorajo, Tokushima (JP)

(73) Assignee: OTSUKA CHEMICAL CO., LTD., Osaka (JP)

( * ) Notice: Subject to any disclaimer, the term of this patent is extended or adjusted under 35 U.S.C. 154(b) by 278 days.

(21) Appl. No.: 15/534,234

(22) PCT Filed: Dec. 11, 2014

(86) PCT No.: PCT/JP2014/082816
§ 371 (c)(1),
(2) Date: Jun. 8, 2017

(87) PCT Pub. No.: WO2016/092664
PCT Pub. Date: Jun. 16, 2016

(65) Prior Publication Data
US 2017/0330700 A1 Nov. 16, 2017

(51) Int. Cl.
| | |
|---|---|
| H01G 11/62 | (2013.01) |
| H01G 11/60 | (2013.01) |
| C07C 211/62 | (2006.01) |
| C01B 25/455 | (2006.01) |
| C01D 7/00 | (2006.01) |
| C01D 13/00 | (2006.01) |
| C01G 28/00 | (2006.01) |
| C01G 30/00 | (2006.01) |

(52) U.S. Cl.
CPC ............ H01G 11/62 (2013.01); C07C 211/62 (2013.01); H01G 11/60 (2013.01); C01B 25/455 (2013.01); C01D 7/00 (2013.01); C01D 13/00 (2013.01); C01G 28/007 (2013.01); C01G 30/006 (2013.01); Y02E 60/13 (2013.01)

(58) Field of Classification Search
CPC ................................ H01G 11/62; H01G 11/60
See application file for complete search history.

(56) References Cited

U.S. PATENT DOCUMENTS

| | | | |
|---|---|---|---|
| 9,601,279 B2 * | 3/2017 | Takahashi | H01M 10/0568 |
| 2006/0223995 A1 | 10/2006 | Uchimura et al. | |
| 2007/0042271 A1 | 2/2007 | Nishida et al. | |
| 2011/0123873 A1 | 5/2011 | Nishida et al. | |
| 2013/0004860 A1 | 1/2013 | Nishida et al. | |
| 2013/0075647 A1 * | 3/2013 | Gadkaree | H01G 9/035 |
| | | | 252/62.2 |
| 2013/0277598 A1 * | 10/2013 | Gadkaree | H01G 9/035 |
| | | | 252/62.2 |
| 2015/0221451 A1 | 8/2015 | Takahashi et al. | |

FOREIGN PATENT DOCUMENTS

| | | |
|---|---|---|
| JP | 3-58526 | 9/1991 |
| JP | 8-31401 | 3/1996 |
| JP | 2000-58397 | * 2/2000 |
| JP | 2000-058397 | 2/2000 |
| JP | 2003-173936 | 6/2003 |
| JP | 2004-47969 | 2/2004 |
| JP | 2004-207451 | 7/2004 |
| JP | 2006-278167 | 10/2006 |
| JP | 2007-077046 | 3/2007 |
| JP | 2007-106753 | 4/2007 |
| JP | 2007-112811 | 5/2007 |
| JP | 2008-210871 | 9/2008 |
| JP | 2010-171087 | 8/2010 |
| JP | 2014-195017 | 10/2014 |
| WO | 2014/038343 | 3/2014 |
| WO | WO 2014/038343 | * 3/2014 |

OTHER PUBLICATIONS

Extended European Search Report dated Jun. 19, 2018 in corresponding European Patent Application No. 14908067.3.*
International Search Report dated Mar. 10, 2015 in International Application No. PCT/JP2014/082816.
International Preliminary Report on Patentability dated Jun. 13, 2017 in International Application No. PCT/JP2014/082816.

* cited by examiner

Primary Examiner — C Melissa Koslow
(74) Attorney, Agent, or Firm — Wenderoth, Lind & Ponack, L.L.P.

(57) ABSTRACT

The present invention provides a nonaqueous electrolytic solution that provides an electric double layer capacitor having excellent durability. The nonaqueous electrolytic solution of the present invention is a nonaqueous electrolytic solution for electric double layer capacitors prepared by dissolving a quaternary ammonium salt as an electrolyte in a nonaqueous solvent, and the nonaqueous electrolytic solution has an alkali metal cation concentration of 0.1 to 30 ppm.

6 Claims, No Drawings

NONAQUEOUS ELECTROLYTIC SOLUTION FOR ELECTRIC DOUBLE LAYER CAPACITORS

TECHNICAL FIELD

The present invention relates to a nonaqueous electrolytic solution for electric double layer capacitors and to an electric double layer capacitor.

BACKGROUND ART

Electric double layer capacitors (EDLCs) are power storage devices that store electric power by using a phenomenon in which ions in an electrolytic solution form an electric double layer due to physical adsorption to an electrode when an electric field is applied to the electrolytic solution. As compared with secondary batteries such as lithium-ion batteries that generate electricity by a chemical reaction, the EDLCs have a higher charging and discharging speed and thus are widely used in uninterruptible power supply systems (UPSs), for example. In recent years, social demands for environmental consciousness and energy efficiency have become more severe, and EDLCs with the above-mentioned properties have been more widely, increasingly demanded as temporary electric power storage apparatuses for energy recovery and auxiliary electric power in automobiles and the like, as temporary electric power storage apparatuses for wind power energy, and as electric power supplies for copy machines or similar machines to return from a standby condition. For the reasons, EDLCs are one of the most attractive power storage devices.

In recent years, electrochemical devices including batteries and capacitors are required to have much higher output density and energy density, and organic electrolytic solutions (nonaqueous electrolytic solutions) have been more widely used than aqueous electrolytic solutions from the viewpoint of voltage endurance.

Examples of known and widely used organic electrolytic solutions include an electrolytic solution prepared by dissolving a solid ammonium salt (electrolyte) such as a linear aliphatic ammonium salt, for example, a tetraethylammonium salt or a triethylmethylammonium salt in an organic solvent such as propylene carbonate (Patent Literature 1); and an electrolytic solution prepared by dissolving a cyclic aliphatic ammonium salt such as an N-ethyl-N-methyl pyrrolidinium salt (Patent Literature 2) or a spiro-(1,1)-bipiperidinium salt (Patent Literature 3) in an organic solvent soon as propylene carbonate. However, the electrolytic solutions have insufficient durability when used in electric double layer capacitors.

CITATION LIST

Patent Literature

Patent Literature 1: JP 03-58526 B
Patent Literature 2: JP 08-31401 B
Patent Literature 3: JP 2008-210871 A

SUMMARY OF INVENTION

Technical Problem

In view of the above circumstances, an object of the present invention is to provide a nonaqueous electrolytic solution that provides an electric double layer capacitor having excellent durability.

Solution to Problem

To develop an electrolyte and an electrolytic solution for capacitors that achieve the above objective, the present inventors conducted intensive investigations and found that, when a nonaqueous electrolytic solution containing a quaternary ammonium salt has an alkali metal cation concentration of 0.1 to 30 ppm, an electric double layer capacitor produced using the nonaqueous electrolytic solution has excellent durability. Based on this finding, the present inventors completed the present invention.

That is, the present invention encompasses the following aspects.

(1) A nonaqueous electrolytic solution for electric double layer capacitors prepared by dissolving a quaternary ammonium salt represented by the general formula (I):

$$Q^+X^- \quad (I)$$

(wherein $Q^+$ represents a quaternary ammonium cation, $X^-$ represents a counter ion selected from the group consisting of $PF_6^-$, $BF_4^-$, $AsF_6^-$, $N(CF_3SO_3)_2^-$, $SbF_6^-$, and $RfSO_3^-$ (Rf is a fluoroalkyl group having 1 to 8 carbon atoms)) as an electrolyte in a nonaqueous solvent, the quaternary ammonium salt excluding spiro quaternary ammonium tetrafluoroborate, the nonaqueous electrolytic solution having an alkali metal cation concentration of 0.1 to 30 ppm.

(2) The nonaqueous electrolytic solution according to the above (1), wherein the alkali metal cation concentration is more than 10 ppm and not more than 30 ppm.

(3) The nonaqueous electrolytic solution according to the above (1) or (2), wherein the alkali metal cation concentration is 12 to 30 ppm.

(4) The nonaqueous electrolytic solution according to any one of the above (1) to (3), wherein the alkali metal cation is a sodium ion and/or a potassium ion.

(5) The nonaqueous electrolytic solution according to any one of the above (1) to (4), wherein the quaternary ammonium cation is tetraalkyl ammonium or pyrrolidinium.

(6) The nonaqueous electrolytic solution according to any one of the above (1) to (5), wherein the quaternary ammonium cation is N-ethyl-N-methyl pyrrolidinium.

(7) The nonaqueous electrolytic solution according to any one of the above (1) to (5), wherein the quaternary ammonium cation is N,N,N-triethyl-N-methyl ammonium.

(8) The nonaqueous electrolytic solution according to any one of the above (1) to (7), wherein the $X^-$ in the general formula (I) is $BF_4^-$.

(9) The nonaqueous electrolytic solution according to any one of the above (1) to (8), wherein the nonaqueous solvent is at least one solvent selected from the group consisting of propylene carbonate, ethylene carbonate, butylane carbonate, sulfolane, methylsulfolane, dimethyl carbonate, ethyl methyl carbonate, and diethyl carbonate.

(10) An electric double layer capacitor comprising the nonaqueous electrolytic solution according to any one of the above (1) to (9) as an electrolytic solution.

Advantageous Effects of Invention

Using the nonaqueous electrolytic solution of the present invention, a highly durable electric double layer capacitor that is less prone to capacity decrease (capacity deterioration) and resistance increase over a long period of time can be produced.

DESCRIPTION OF EMBODIMENTS

The present invention will now be described in detail.

The nonaqueous electrolytic solution of the present invention is a nonaqueous electrolytic solution for electric double layer capacitors prepared by dissolving a quaternary ammonium salt represented by the general formula (I) as an electrolyte in a nonaqueous solvent. The nonaqueous electrolytic solution of the present invention has an alkali metal cation concentration of 0.1 to 30 ppm.

When she nonaqueous electrolytic solution has an alkali metal cation concentration of 0.1 to 30 ppm, electric double layer capacitors produced using the nonaqueous electrolytic solution have excellent durability. In cases where two or more kinds of alkali metal ions are contained, the total concentration should be within this range.

When the alkali metal cation concentration is more than 30 ppm, the electric double layer capacitor produced using the nonaqueous electrolytic solution can be prone to decrease in the electric capacity (capacity deterioration). Also, when the alkali metal cation concentration is more than 30 ppm, the electric double layer capacitor produced using the nonaqueous electrolytic solution can be prone to increase in the leakage of current or the like.

The alkali metal cation concentration in the nonaqueous electrolytic solution is preferably more than 10 ppm and not more than 30 ppm, and more preferably 12 to 30 ppm. When the alkali metal cation concentration is within this range, an electric double layer capacitor produced using the nonaqueous electrolytic solution becomes a highly durable electric double layer capacitor that is less prone to capacity decrease (capacity deterioration) and resistance increase.

Examples of the alkali metal cation include lithium ion, sodium ion, potassium ion, etc. The alkali metal cations may be used alone or in combination of two or more kinds thereof. Preferably, the alkali metal ion is sodium ion, potassium ion, or both thereof. In the present invention, the total concentration of sodium ions and potassium ions in the nonaqueous electrolytic solution is preferably 0.1 to 30 ppm.

The method for preparing a nonaqueous electrolytic solution of which the alkali metal cation concentration is controlled to be within this range is not particularly limited. For example, the alkali metal cation concentration in the nonaqueous electrolytic solution may be adjusted by adjusting the alkali metal cation concentration in the nonaqueous solvent and/or the electrolyte, which are components of the nonaqueous electrolytic solution, or by separately adding an alkali metal to the nonaqueous electrolytic solution. Preferred is, for example, the method in which the alkali metal cation concentration in the nonaqueous electrolytic solution is adjusted by adjusting the alkali metal cation concentration in the quaternary ammonium salt used for the electrolytic solution. For example, the alkali metal cation concentration in the quaternary ammonium salt used for the preparation of the electrolytic solution is preferably about 0.2 to 300 ppm, and more preferably about 0.5 to 120 ppm. Examples of the method for adjusting the alkali metal cation concentration in the quaternary ammonium salt include a method in which, in the production of the quaternary ammonium salt represented by the general formula (I) as an electrolyte, an alkali metal salt is used in the salt exchange to control the number of equivalents of the reagent; a method in which the electrolyte (the quaternary ammonium salt represented by the general formula (I)) is dissolved in a poor solvent for an alkali metal (a solvent in which an alkali metal has a low solubility) and then the resulting solution containing the electrolyte is filtered to remove the alkali metal undissolved in the poor solvent; and the like. By such a method, a quaternary ammonium salt represented by the general formula (I) having an alkali metal cation concentration of usually about 0.2 to 300 ppm, and preferably about 0.5 to 120 ppm can be obtained. By dissolving the thus obtained quaternary ammonium salt represented by the general formula (I) in a highly pure nonaqueous solvent (for example, having a purity of about 99.99% of higher) at a concentration of about 0.1 to 3 mol/L, for example, a nonaqueous electrolytic solution having an alkali metal cation concentration of 0.1 to 30 ppm can be obtained.

In particular, as the method for adjusting the alkali metal cation concentration in the quaternary ammonium salt represented by the general formula (I), preferred is the method in which the electrolyte is dissolved in a poor solvent for an alkali metal (a solvent in which an alkali metal has a low solubility) and then the alkali metal undissolved in the poor solvent is removed by filtration. The reasons are that the operation is easy and that numeric values can easily be controlled. When this method is used to adjust the alkali metal cation concentration, the alkali metal cation concentration in the quaternary ammonium salt represented by the general formula (I) depends on the poor solvent used, filtration temperature, etc. Preferred examples of the poor solvent include isopropyl alcohol, propylene carbonate, dichloromethane, etc. The filtration temperature is, for example, preferably about −10 to 50° C., and mere preferably about 0 to 25° C. The method of the filtration is not particularly limited and a conventional method (under atmospheric pressure, increased pressure, or reduced pressure) may be employed. The amount of the poor solvent used is not particularly limited, and may be about 1 to 10 times the amount by mass of the quaternary ammonium salt represented by the general formula (I). For example, when propylene carbonate is used as the poor solvent, preferred is a method in which the electrolyte (in the quaternary ammonium salt represented by the general formula (I)) is dissolved in propylene carbonate at about 5 to 50° C., and the resulting solution is filtered under atmospheric pressure. When the quaternary ammonium salt represented by the general formula (I) obtained by such a method is used for preparing a nonaqueous electrolytic solution, the alkali metal cation concentration in the nonaqueous electrolytic solution can usually be controlled to be within 0.1 to 30 ppm.

The quantity of alkali metal cations contained in the quaternary ammonium salt and the nonaqueous electrolytic solution can be determined by a publicly known method, such as ion chromatography. In the cases where the measurement method is ion chromatography, for example, the conditions described in Examples etc. may be adopted, for example.

The nonaqueous solvent used in the present invention is not particularly limited, and examples thereof include propylene carbonate, ethylene carbonate, butylene carbonate, sulfolane, methylsulfolane, dimethyl carbonate, ethyl methyl carbonate, diethyl carbonate, γ-butyrolactone, and acetonitrile. These nonaqueous solvents may be used alone or as a mixture of two or more kinds thereof. In particular, preferred is at least one kind selected from propylene carbonate, ethylene carbonate, butylene carbonate, sulfolane, methylsulfolane, dimethyl carbonate, ethyl methyl carbonate, and diethyl carbonate, and more preferred is propylene carbonate. As the nonaqueous solvent, a commercially available compound may be used as it is or after further purification by any appropriate method.

The concentration of the quaternary ammonium salt represented by the general formula (I) as an electrolyte in the nonaqueous electrolytic solution is preferably about 0.1 to 3 mol/L, and particularly preferably about 0.5 to 1.5 mol/L. When the electrolyte concentration is within such a range, the nonaqueous electrolytic solution has a high electric conductivity, which is preferable. Also, when the electrolyte concentration is within such a range, increase in the internal resistance of the electric double layer capacitor produced using the nonaqueous electrolytic solution can more effectively be reduced. Furthermore, when the electrolyte concentration is within such a range, salt precipitation in the nonaqueous electrolytic solution is less likely to occur even at low temperatures, for example, and thus the nonaqueous electrolytic solution is preferable for use at low temperatures.

In the present invention, a quaternary ammonium salt represented by the above general formula (I) is used as an electrolyte.

In the above general formula (I), $Q^+$ represents a quaternary ammonium cation. $X^-$ represents a counter ion selected from the group consisting of $PF_6^-$, $BF_4^-$, $AsF_6^-$, $N(CF_3SO_3)_2^-$, $SbF_6^-$, and $RfSO_3^-$ (Rf is a fluoroalkyl group having 1 to 8 carbon atoms).

X is preferably $BF_4^-$.

As the quaternary ammonium cation (a quaternary ammonium group) represented, by $Q^+$, those obtained by quaternization of a tertiary amine with, for example, an alkyl group, a cycloalkyl group, an aryl group, an aralkyl group, etc. may be used. The hydrocarbon moiety constituting the quaternary ammonium cation may have a hydroxyl group, an amino group, a nitro group, a cyano group, a carbonyl group, an ether group, an aldehyde group, etc. bound thereto.

Examples of the quaternary ammonium cation used in the present invention include a tetraalkylammonium ion obtained by quaternization of the nitrogen of a trialkylamine, a pyrrolidinium ion obtained by quaternization of the nitrogen of a pyrrolidine ring, a spiro quaternary ammonium ion, a morpholinium ion obtained by quaternization of the nitrogen of a morpholine ring, an imidazolinium ion obtained by quaternization of the nitrogen of an imidazoline ring, a pyrimidinium ion obtained by quaternization of the nitrogen of a tetrahydropyrimidine ring, a piperazinium ion obtained by quaternization of the nitrogen of a piperazine ring, a piperidinium ion obtained by quaternization of the nitrogen of a piperidine ring, a pyridinium ion obtained by quaternization of the nitrogen of a pyridine ring, and a imidazolium ion obtained by quaternization of the nitrogen of an imidazole ring.

Examples of the quaternary ammonium cation obtained by quaternization of the nitrogen of a trialkylamine (the tetraalkylammonium ion) include tetramethylammonium, ethyltrimethylammonium, diethyldimethylammonium, N,N,N-triethyl-N-methylammonium, tetraethylammonium, trimethyl-n-propylammonium, trimethylisopropylammonium, ethyldimethyl-n-propylammonium, ethyldimethylisopropylammonium, diethylmethyl-n-propyl ammonium, diethylmethylisopropyl ammonium, dimethyldi-n-propylammonium, dimethyl-n-propylisopropylammonium, dimethyldiisopropylammonium, triethyl-n-propylammonium, n-butyltrimethylammonium, isobutyltrimethylammonium, t-butyltrimethylammonium, triethylisopropylammonium, ethylmethyldi-n-propylammonium, ethylmethyl-n-propylisopropylammonium, ethylmethyldiisopropylammonium, n-butylethyldimethylammonium, isobutylethyldimethylammonium, t-butylethyldimethylammonium, diethyldi-n-propylammonium, diethyl-n-propylisopropylammonium, diethyldiisopropylammonium, methyltri-n-propylammonium, methyldi-n-propylisopropylammonium, methyl-n-propyldi-isopropylammonium, n-butyltriethylammonium, isobutyltriethylammonium, t-butyltriethylammonium, di-n-buthyldimethylammonium, diisobutyldimethylammonium, di-t-buthyldimethylammonium, n-butylisobutyldimethylammonium, n-butyl-t-buthyldimethylammonium, isobutyl-t-buthyldimethylammonium, etc.

Examples of the quaternary ammonium cation obtained by quaternization of the nitrogen of a pyrrolidine ring (the pyrrolidinium ion) include N,N-dimethylpyrrolidinium, N-ethyl-N-methylpyrrolidinium, N,N-diethylpyrrolidinium, 1,1,2-trimethylpyrrolidinium, 1,1,3-trimethylpyrrolidinium, 1-ethyl-1,2-dimethylpyrrolidinium, 1-ethyl-1,3-dimethylpyrrolidinium, 2-ethyl-1,1-dimethylpyrrolidinium, 3-ethyl-1,1-dimethylpyrrolidinium, 1,1-diethyl-2-methylpyrrolidinium, 1,1-diethyl-3-methylpyrrolidinium, 1,2-diethyl-1-methylpyrrolidinium, 1,3-diethyl-1-methylpyrrolidinium, 1,1,2-triethylpyrrolidinium, 1,1,3-triethylpyrrolidinium, 1,1,2,2-tetramethylpyrrolidinium, 1,1,2,3-tetramethylpyrrolidinium, 1,1,2,4-tetramethylpyrrolidinium, 1,1,2,5-tetramethylpyrrolidinium, 1,1,3,4-tetramethylpyrrolidinium, 1,1,3,3-tetramethylpyrrolidinium, 2-ethyl-1,1,2-trimethylpyrrolidinium, 2-ethyl-1,1,3-trimethylpyrrolidinium, 3-ethyl-1,1,2-trimethylpyrrolidinium, 3-ethyl-1,1,3-trimethylpyrrolidinium, 2-ethyl-1,1,4-trimethylpyrrolidinium, 4-ethyl-1,1,2-trimethylpyrrolidinium, 2-ethyl-1,1,5-trimethylpyrrolidinium, 3-ethyl-1,1,4-trimethylpyrrolidinium, 1-ethyl-1,2,2-trimethylpyrrolidinium, 1-ethyl-1,2,3-trimethylpyrrolidinium, 1-ethyl-1,3,3-trimethylpyrrolidinium, 1-ethyl-1,2,4-trimethylpyrrolidinium, 1-ethyl-1,2,5-trimethylpyrrolidinium, 1-ethyl-1,3,4-trimethylpyrrolidinium, 2,2-diethyl-1,1-dimethylpyrrolidinium, 2,3-diethyl-1,1-dimethylpyrrolidinium, 3,3-diethyl-1,1-dimethylpyrrolidinium, 2,4-diethyl-1,1-dimethylpyrrolidinium, 2,5-diethyl-1,1-dimethylpyrrolidinium, 3,4-diethyl-1,1-dimethylpyrrolidinium, 1,2-diethyl-1,2-dimethylpyrrolidinium, 1,2-diethyl-1,3-dimethylpyrrolidinium, 1,3-diethyl-1,2-dimethylpyrrolidinium, 1,3-diethyl-1,3-dimethylpyrrolidinium, 1,2-diethyl-1,4-dimethylpyrrolidinium, 1,4-diethyl-1,2-dimethylpyrrolidinium, 1,2-diethyl-1,5-dimethylpyrrolidinium, 1,3-diethyl-1,4-dimethylpyrrolidinium, 1,1,2,2,3-pentamethylpyrrolidinium, 1,1,2,2,4-pentamethylpyrrolidinium, 1,1,2,2,5-pentamethylpyrrolidinium, 1,1,2,3,4-pentamethylpyrrolidinium, 1,1,2,3,5-pentamethylpyrrolidinium, 1,1,3,3,4-pentamethylpyrrolidinium, 1,1,3,3,5-pentamethylpyrrolidinium, 1-ethyl-1,2,2,3-tetramethylpyrrolidinium, 1-ethyl-1,2,2,4-tetramethylpyrrolidinium, 1-ethyl-1,2,2,5-tetramethylpyrrolidinium, 1-ethyl-1,2,3,4-tetramethylpyrrolidinium, 1-ethyl-1,2,3,5-tetramethylpyrrolidinium, 1-ethyl-1,2,4,5-tetramethylpyrrolidinium, 1-ethyl-1,3,3,4-tetramethylpyrrolidinium, 1-ethyl-1,3,3,5-tetramethylpyrrolidinium, 2-ethyl-1,1,2,3-tetramethylpyrrolidinium, 2-ethyl-1,1,2,4-tetramethylpyrrolidinium, 2-ethyl-1,1,2,5-tetramethylpyrrolidinium, 2-ethyl-1,1,3,3- tetramethylpyrrolidinium, 2-ethyl-1,1,3,4-tetramethylpyrrolidinium, 2-ethyl-1,1,3,5-tetramethylpyrrolidinium, 2-ethyl-1,1,4,4-tetramethylpyrrolidinium, 2-ethyl-1,1,4,5-tetramethylpyrrolidinium, 2-ethyl-1,1,5,5-tetramethylpyrrolidinium, 3-ethyl-1,1,2,2-tetramethylpyrrolidinium, 3-ethyl-1,1,2,3-tetramethylpyrrolidinium, 3-ethyl-1,1,2,4-tetramethylpyrrolidinium, 3-ethyl-1,1,2,5-tetramethylpyrrolidinium, 3-ethyl-1,1,3,4-tetramethylpyrrolidinium, 3-ethyl-1,1,4,4-tetramethylpyrrolidinium, 3-ethyl-1,1,4,5-tetramethylpyrrolidinium, 1,1,2,2,3,3-hexamethylpyrrolidinium, 1,1,2,2,3,4-hexamethylpyrrolidinium, 1,1,2,2,3,5-hexamethylpyrrolidinium, 1,1,2,2,4,4-hexamethylpyrrolidinium, 1,1,2,2,4,5-hexamethylpyrrolidinium, 1,1,2,2,5,5-hexamethylpyrrolidinium, 1,1,2,3,3,4-hexamethylpyrrolidinium, 1,1,2,3,3,5-hexamethylpyrrolidinium, 1,1,2,3,4,4-hexamethylpyrrolidinium, 1,1,2,3,5,5-hexamethylpyrrolidinium, 1,1,2,3,4,5-hexamethylpyrrolidinium, etc.

Examples of the a spiro quaternary ammonium cation include spiro-(1,1')-bipyrrolidinium, 2-methylspiro-(1,1')-bipyrrolidinium, 3-methylspiro-(1,1')-bipyrrolidinium, 2,2-dimethylspiro-(1,1')-bipyrrolidinium, 2,3-dimethylspiro-(1,1')-bipyrrolidinium, 3,3-dimethylspiro-(1,1')-bipyrrolidinium, 2,4-dimethylspiro-(1,1')-bipyrrolidinium, 2,5-dimethylspiro-(1,1')-bipyrrolidinium, 3,4-dimethylspiro-(1,1')-bipyrrolidinium, 2,2'-dimethyl-spiro-(1,1')-bipyrrolidinium, 2,3'-dimethylspiro-(1,1')-bipyrrolidinium, 2,4'-dimethylspiro-(1,1')-bipyrrolidinium, 2,5'-dimethylspiro-(1,1')-bipyrrolidinium, 2,3,4-trimethylspiro-(1,1')-bipyrrolidinium, 2,3,5-trimethylspiro-(1,1')-bipyrrolidinium, 3,4,5-trimethylspiro-(1,1')-bipyrrolidinium, 2,3,2'-trimethylspiro-(1,1')-bipyrrolidinium, 2,3,3'-trimethylspiro-(1,1')-bipyrrolidinium, 2,3,4'-trimethylspiro-(1,1')-bipyrrolidinium, 2,3,5'-trimethylspiro-(1,1')-bipyrrolidinium, 3,4,2'-trimethylspiro-(1,1')-bipyrrolidinium, 3,4,3'-trimethylspiro-(1,1')-bipyrrolidinium, 3,4,4'-trimethylspiro-(1,1')-bipyrrolidinium, 3,4,5'-trimethylspiro-(1,1')-bipyrrolidinium, 2-ethylspiro-(1,1')-bipyrrolidinium, etc.

Examples of the quaternary ammonium cation obtained by quaternization of the nitrogen of a morpholine ring (the morpholinium ion) include N,N-dimethylmorpholinium, N-ethyl-N-methylmorpholinium, N,N-diethylmorpholinium, 3,4,4-trimethylmorpholinium, 2,4,4-trimethylmorpholinium, 3-ethyl-4,4-dimethylmorpholinium, 2-ethyl-4,4-dimethylmorpholinium, 3,4-dimethyl-4-ethylmorpholinium, 2,4-dimethyl-4-ethylmorpholinium, 3-methyl-4,4-diethylmorpholinium, 2-methyl-4,4-diethylmorpholinium, 3,4-diethyl-4-methylmorpholinium, 2,4-diethyl-4-methylmorpholinium, 3,4,4-triethylmorpholinium, 2,4,4-triethylmorpholinium, 3,3,4,4-tetramethylmorpholinium, 2,3,4,4-tetramethylmorpholinium, 2,4,4,5-tetramethylmorpholinium, 3,4,4,5-tetramethylmorpholinium, 2,4,4,4-tetramethylmorpholinium, 2,4,4,6-tetramethylmorpholinium, 2,4,4-trimethyl-3-ethylmorpholinium, 2-ethyl-3,4,4-trimethylmorpholinium, 2,4,4-trimethyl-5-ethylmorpholinium, 2-ethyl-4,4,5-trimethylmorpholinium, 3-ethyl-4,4,5-trimethylmorpholinium, 2-ethyl-4,4,6-trimethylmorpholinium, 2,3-dimethyl-4,4-diethylmorpholinium, 2,5-dimethyl-4,4-diethylmorpholinium, 3,5-dimethyl-4,4-diethylmorpholinium, 2,6-dimethyl-4,4-diethylmorpholinium, 2,4-dimethyl-3,4-diethylmorpholinium, 2,4-diethyl-3,4-dimethylmorpholinium, 2,4-dimethyl-4,5-diethylmorpholinium, 2,4-diethyl-4,5-dimethylmorpholinium, 3,4-diethyl-4,5-dimethylmorpholinium, 2,4-diethyl-4,6-dimethylmorpholinium, 2,3-diethyl-4,4-dimethylmorpholinium, 2,5-diethyl-4,4-dimethylmorpholinium, 3,5-diethyl-4,4-dimethylmorpholinium, 2,6-diethyl-4,4-dimethylmorpholinium, 2,3,4,4,6-pentamethylmorpholinium, 2,3,4,4,5-pentamethylmorpholinium, 2,4,4,6-tetramethyl-3-ethylmorpholinium, 2,4,4,5-tetramethyl-3-ethylmorpholinium, 2-ethyl-3,4,4,6-tetramethylmorpholinium, 2-ethyl-3,4,4,5-tetramethylmorpholinium, 2,3,4,4,5,6-hexamethylmorpholinium, etc.

Examples of the quaternary ammonium cation obtained by quaternization of the nitrogen of an imidazoline ring (the imidazolinium ion) include N,N'-dimethylimidazolinium, N-ethyl-N'-methylimidazolinium, N,N'-dimethylimidazolinium, 1,2,3-trimethylimidazolinium, 1,3,4-trimethylimidazolium, 1-ethyl-2,3-dimethylimidazolinium, 1-ethyl-3,4-dimethylimidazolinium, 1-ethyl-3,5-dimethylimidazolinium, 2-ethyl-1,3-dimethylimidazolinium, 4-ethyl-1,3-dimethylimidazolinium, 1,2-diethyl-3-methylimidazolinium, 1,4-diethyl-3-methylimidazolinium, 1,5-diethyl-3-methylimidazolinium, 1,3-diethyl-2-methylimidazolinium, 1,3-diethyl-4-methylimidazolinium, 1,2,3-triethylimidazolinium, 1,3,4-triethylimidazolinium, 1,2,3,4-tetramethylimidazolinium, 1-ethyl-2,3,4-trimethylimidazolinium, 1-ethyl-2,3,5-trimethylimidazolinium, 1-ethyl-3,4,5-trimethylimidazolinium, 2-ethyl-1,3,4-trimethylimidazolinium, 4-ethyl-1,2,3-trimethylimidazolinium, 1,2-diethyl-3,4-dimethylimidazolinium, 1,3-diethyl-2,4-dimethylimidazolinium, 1,4-diethyl-2,3-dimethylimidazolinium, 2,4-diethyl-1,3-dimethylimidazolinium, 4,5-diethyl-1,3-dimethylimidazolinium, 1,2,3-triethyl-4-methylimidazolinium, 1,2,4-triethyl-3-methylimidazolinium, 1,2,5-triethyl-3-methylimidazolinium, 1,3,4-triethyl-2-methylimidazolinium, 1,3,4-triethyl-5-methylimidazolinium, 1,4,5-triethyl-3-methylimidazolinium, 1,2,3,4,5-pentamethylimidazolinium, etc.

Examples of the quaternary ammonium cation obtained by quaternization of the nitrogen of a tetrahydropyrimidine ring (the pyrimidinium ion) include N,N'-dimethyltetrahydropyrimidinium, N-ethyl-N'-methyltetrahydropyrimidinium, N,N'-diethyltetrahydropyrimidinium, 1,2,3-trimethyltetrahydropyrimidinium, 1,3,4-trimethyltetrahydropyrimidinium, 1,3,5-trimethyltetrahydropyrimidinium, 1-ethyl-2,3-dimethyltetrahydropyrimidinium, 1-ethyl-3,4-dimethyltetrahydropyrimidinium, 1-ethyl-3,5-dimethyltetrahydropyrimidinium, 1-ethyl-3,6-dimethyltetrahydropyrimidinium, 2-ethyl-1,3-dimethyltetrahydropyrimidinium, 4-ethyl-1,3-dimethyltetrahydropyrimidinium, 5-ethyl-1,3-dimethyltetrahydropyrimidinium, 1,2,3,4-tetramethyltetrahydropyrimidinium, 1,2,3,5-tetramethyltetrahydropyrimidinium, 1-ethyl-2,3,4-trimethyltetrahydropyrimidinium, 1-ethyl-2,3,5-trimethyltetrahydropyrimidinium, 1-ethyl-2,3,6-trimethyltetrahydropyrimidinium, 2-ethyl-1,3,4-trimethyltetrahydropyrimidinium, 2-ethyl-1,3,5-trimethyltetrahydropyrimidinium, 4-ethyl-1,2,3-trimethyltetrahydropyrimidinium, 4-ethyl-1,3,5- trimethyltetrahydropyrimidinium, 4-ethyl-1,3,6-trimethyltetrahydropyrimidinium, 5-ethyl-1,2,3-trimethyltetrahydropyrimidinium, 5-ethyl-1,3,4-trimethyltetrahydropyrimidinium, 1,2-diethyl-3,4-dimethyltetrahydropyrimidinium, 1,2-diethyl-3,5-dimethyltetrahydropyrimidinium, 1,2-diethyl-3,6-dimethyltetrahydropyrimidinium, 1,3-diethyl-2,4-dimethyltetrahydropyrimidinium, 1,3-diethyl-2,5-dimethyltetrahydropyrimidinium, 1,4-diethyl-2,3-dimethyltetrahydropyrimidinium, 1,4-diethyl-3,5-dimethyltetrahydropyrimidinium, 1,4-diethyl-3,6-dimethyltetrahydropyrimidinium, 1,5-diethyl-2,3-dimethyltetrahydropyrimidinium, 1,5-diethyl-3,4-dimethyltetrahydropyrimidinium, 1,5-diethyl-3,6-dimethyltetrahydropyrimidinium, 2,4-diethyl-1,3-dimethyltetrahydropyrimidinium, 2,5-diethyl-1,3-dimethyltetrahydropyrimidinium, 4,5-diethyl-1,3-dimethyltetrahydropyrimidinium, 4,6-diethyl-1,3-dimethyltetrahydropyrimidinium, 1,2,3,4,5-pentamethyltetrahydropyrimidinium, 1,2,3,4,6-pentamethyltetrahydropyrimidinium, 1,2,3,4,5,6-hexamethyltetrahydropyrimidinium, 5-methyl-1,5-diazabicyclo[4.3.0]-5-nonenium, 5-ethyl-1,5-diazabicyclo[4.3.0]-5-nonenium, 5-methyl-1,5-diazabicyclo[5.4.0]-5-undecenium, 5-ethyl-1,5-diazabicyclo[5.4.0]-5-undecenium, etc.

Examples of the quaternary ammonium cation obtained by quaternization of the nitrogen of a piperazine ring (the piperazinium ion) include N,N,N',N'-tetramethylpiperazinium, N-ethyl-N,N',N'-trimethylpiperazinium, N,N-diethyl-N',N'-dimethylpiperazinium, N,N,N'-triethyl-N'-methylpiperazinium, N,N,N',N'-tetraethylpiperazinium, 1,1,2,4,4-pentamethylpiperazinium, 1,1,3,4,4-pentamethylpiperazinium, 1,1,2,3,4,4-hexamethylpiperazinium, 1,1,2,4,4,5-hexamethylpiperazinium, 1,1,2,4,4,6-hexamethylpiperazinium, 1,1,3,4,4,5-hexamethylpiperazinium, 1-ethyl-1,2,4,4-tetramethylpiperazinium, 1-ethyl-1,3,4,4-tetramethylpiperazinium, 2-ethyl-1,1,4,4-tetramethylpiperazinium, 1-ethyl-1,2,4,4-tetramethylpiperazinium, 1-ethyl-1,3,4,4-tetramethylpiperazinium, 1,1-diethyl-2,4,4-trimethylpiperazinium, 1,4-diethyl-1,2,4-trimethylpiperazinium, 1,2-diethyl-1,4,4-trimethylpiperazinium, 1,3-diethyl-1,4,4-trimethylpiperazinium, etc.

Examples of the quaternary ammonium cation obtained by quaternization of the nitrogen of a piperidine ring (the piperidinium ion) include N,N-dimethylpiperidinium, N-ethyl-N-methylpiperidinium, N,N-diethylpiperidinium, 1,1,2-trimethylpiperidinium, 1,1,3-trimethylpiperidinium, 1,1,4-trimethylpiperidinium, 1,2,2-tetramethylpiperidinium, 1,1,2,3-tetramethylpiperidinium, 1,1,2,4-tetramethylpiperidinium, 1,1,2,5-tetramethylpiperidinium, 1,1,2,6-tetramethylpiperidinium, 1,1,3,3-tetramethylpiperidinium, 1,1,3,4-tetramethylpiperidinium, 1,1,3,5-tetramethylpiperidinium, 1-ethyl-1,2-dimethylpiperidinium, 1-ethyl-1,3-dimethylpiperidinium, 1-ethyl-1,4-dimethylpiperidinium, 1-ethyl-1,2,3-trimethylpiperidinium, 1-ethyl-1,2,4-trimethylpiperidinium, 1-ethyl-1,2,5-trimethylpiperidinium, 1-ethyl-1,2,6-trimethylpiperidinium, 1-ethyl-1,3,4-trimethylpiperidinium, 1-ethyl-1,3,5-trimethylpiperidinium, 1,1-diethyl-2-methylpiperidinium, 1,1-diethyl-3-methylpiperidinium, 1,1-diethyl-4-methylpiperidinium, 1,1-diethyl-2,3-dimethylpiperidinium, 1,1-diethyl-2,4-dimethylpiperidinium, 1,1-diethyl-2,5-dimethylpiperidinium, 1,1-diethyl-2,6-dimethylpiperidinium, 1,1-diethyl-3,4-dimethylpiperidinium, 1,1-diethyl-3,5-dimethylpiperidinium, 2-ethyl-1,1,3-trimethylpiperidinium, 2-ethyl-1,1,4-trimethylpiperidinium, 2-ethyl-1,1,5-trimethylpiperidinium, 2-ethyl-1,1,6-trimethylpiperidinium, 3-ethyl-1,1,2-trimethylpiperidinium, 3-ethyl-1,1,4-trimethylpiperidinium, 3-ethyl-1,1,5-trimethylpiperidinium, 3-ethyl-1,1,6-trimethylpiperidinium, 4-ethyl-1,1,2-trimethylpiperidinium, 4-ethyl-1,1,3-trimethylpiperidinium, 1,2-diethyl-1,3-dimethylpiperidinium, 1-ethyl-1,2,4-trimethylpiperidinium, 1,2-diethyl-1,5-dimethylpiperidinium, 1,2-diethyl-1,6-dimethylpiperidinium, 1,3-diethyl-1,5-dimethylpiperidinium, 1,3-diethyl-1,4-dimethylpiperidinium, 1,3-diethyl-1,6-dimethylpiperidinium, 1,4-diethyl-1,2-dimethylpiperidinium, 1,4-diethyl-1,3-dimethylpiperidinium, 1,1,2-triethyl-3-methylpiperidinium, 1,1,2-triethyl-4-methylpiperidinium, 1,1,2-triethyl-5-methylpiperidinium, 1,1,2-triethyl-6-methylpiperidinium, 1,1,3-triethyl-2-methylpiperidinium, 1,1,3-triethyl-4-methylpiperidinium, 1,1,3-triethyl-5-methylpiperidinium, 1,1,3-triethyl-6-methylpiperidinium, 1,1,4-triethyl-2-methylpiperidinium, 1,1,4-triethyl-3-methylpiperidinium, 2-ethyl-1,1-dimethyl-piperidinium, 3-ethyl-1,1-dimethylpiperidinium, 4-ethyl-1,1-dimethyl-piperidinium, 2,3-diethyl-1,1-dimethylpiperidinium, 2,4-diethyl-1,1-dimethylpiperidinium, 2,5-diethyl-1,1-dimethylpiperidinium, 2,6-diethyl-1,1-dimethylpiperidinium, 3,4-diethyl-1,1-dimethylpiperidinium, 3,5-diethyl-1,1-dimethylpiperidinium, 1,2-diethyl-1-methylpiperidinium, 1,3-diethyl-1-methylpiperidinium, 1,4-diethyl-1-methylpiperidinium, 1,2,3-triethyl-1-methylpiperidinium, 1,2,4-triethyl-1-methylpiperidinium, 1,2,5-triethyl-1-methylpiperidinium, 1,2,6-triethyl-1-methylpiperidinium, 1,3,4-triethyl-1-methylpiperidinium 1,3,5-triethyl-1-methylpiperidinium, 1,1,2-triethylpiperidinium, 1,1,4-triethylpiperidinium, 1,1,2,3-tetraethyl-piperidinium, 1,1,2,4-tetraethylpiperidinium, 1,1,2,5-tetraethylpiperidinium, 1,1,2,6-tetraethylpiperidinium, 1,1,3,4-tetramethylpiperidinium, 1,1,3,5-tetraethylpiperidinium, etc.

Examples of the quaternary ammonium cation obtained by quaternization of the nitrogen of a pyridine ring (the pyridinium ion) include N-methylpyridinium, N-ethylpyridinium, 1,2-dimethylpyridinium, 1,3-dimethylpyridinium, 1,4-dimethylpyridinium, 1-ethyl-2-methylpyridinium, 2-ethyl-1-methylpyridinium, 1-ethyl-3-methylpyridinium, 3-ethyl-1-methylpyridinium, 1-ethyl-4-methylpyridinium, 4-ethyl-1-methylpyridinium, 1,2-diethylpyridinium, 1,3-diethylpyridinium, 1,4-diethylpyridinium, 1,2,3-trimethylpyridinium, 1,2,4-trimethylpyridinium, 1,3,4-trimethylpyridinium, 1,3,5-trimethylpyridinium, 1,2,5-trimethylpyridinium, 1,2,6-trimethylpyridinium, 1-ethyl-2,3-dimethylpyridinium, 1-ethyl-2,4-dimethylpyridinium, 1-ethyl-2,5-dimethylpyridinium, 1-ethyl-2,6-dimethylpyridinium, 1-ethyl-3,4-dimethylpyridinium, 1-ethyl-3,5-dimethylpyridinium, 2-ethyl-1,3-dimethylpyridinium, 2-ethyl-1,4-dimethylpyridinium, 2-ethyl-1,5-dimethylpyridinium, 2-ethyl-1,6-dimethylpyridinium, 3-ethyl-1,2-dimethylpyridinium, 3-ethyl-1,4-dimethylpyridinium, 3-ethyl-1,5-dimethylpyridinium, 3-ethyl-1,6-dimethylpyridinium, 4-ethyl-1,2-dimethylpyridinium, 4-ethyl-1,3-dimethylpyridinium, 1,2-diethyl-3-methylpyridinium, 1,2-diethyl-4-methylpyridinium, 1,2-diethyl-5-methylpyridinium, 1,2-diethyl-6-methylpyridinium, 1,3-diethyl-2-methylpyridinium, 1,3-diethyl-4-methylpyridinium, 1,3-diethyl-5-methylpyridinium, 1,3-diethyl-6-methylpyridinium, 1,4-diethyl-2-methylpyridinium, 1,4-diethyl-3-methylpyridinium, 2,3-diethyl-1- methylpyridinium, 2,4-diethyl-1-methylpyridinium, 2,5-diethyl-1-methylpyridinium, 2,6-diethyl-1-methylpyridinium, 3,4-diethyl-1-methylpyridinium, 3,5-diethyl-1-methylpyridinium, 1,2,3,4,5-pentamethylpyridinium, 1,2,3,4,6-pentamethylpyridinium, 1,2,3,5,6-pentamethylpyridinium, 1,2,3,5,6-hexamethylpyridinium, etc.

Examples of the quaternary ammonium cation obtained by quaternization of the nitrogen of an imidazole ring (the imidazolium ion) include N,N'-dimethylimidazolium, N-ethyl-N'-methylimidazolium, N,N'-diethylimidazolium, 1,2,3-trimethylimidazolium, 1,3,4-trimethylimidazolium, 1-ethyl-2,3-dimethylimidazolium, 1-ethyl-3,4-dimethylimidazolium, 1-ethyl-3,5-dimethylimidazolium, 2-ethyl-1,3-dimethylimidazolium, 4-ethyl-1,3-dimethylimidazolium, 1,2-diethyl-3-methylimidazolium, 1,4-diethyl-3-methylimidazolium, 1,5-diethyl-3-methylimidazolium, 1,3-diethyl-2-methylimidazolium, 1,3-diethyl-4-methylimidazolium, 1,2,3-triethylimidazolium, 1,3,4-triethylimidazolium, 1,2,3,4-tetramethylimidazolium, 1-ethyl-2,3,4-trimethylimidazolium, 1-ethyl-2,3,5-trimethylimidazolium, 1-ethyl-3,4,5-trimethylimidazolium, 2-ethyl-1,3,4-trimethylimidazolium, 4-ethyl-1,2,3-trimethylimidazolium, 1,2-diethyl-3,4-dimethylimidazolium, 1,3-diethyl-1,4-dimethylimidazolium, 1,4-diethyl-2,3-dimethylimidazolium, 1,4-diethyl-2,5-dimethylimidazolium, 2,4-diethyl-1,3-dimethylimidazolium, 4,5-diethyl-1,3-dimethylimidazolium, 1,2,3-triethyl-4-methylimidazolium, 1,2,4-triethyl-3-methylimidazolium, 1,2,5-triethyl-3-methylimidazolium, 1,3,4-triethyl-2-methylimidazolium, 1,3,4-triethyl 5-methylimidazolium, 1,4,5-triethyl-3-methylimidazolium, 1,2,3,4,5-pentamethylimidazolium, etc.

Among them, preferred as the quaternary ammonium cation is a tetraalkylammonium ion or a pyrrolidinium ion. The tetraalkylammonium ion is more preferably N,N,N-triethyl-N-methylammonium. The pyrrolidinium ion is more preferably N-ethyl-N-methylpyrrolidinium. Particularly preferred as the quaternary ammonium cation is N-ethyl-N-methylpyrrolidinium.

As the quaternary ammonium salt represented by the general formula (I), a commercially available compound may be used. Alternatively, the quaternary ammonium salt may be produced by a publicly known method, for example, a method in which a halide salt of a quaternary ammonium obtained by the reaction of a tertiary amine and an alkyl halide is mixed, in any appropriate solvent, with an acid formed of a counter ion represented by $X^-$ in the general formula (I) or an alkali metal salt thereof to allow a reaction (salt exchange) therebetween.

The electrolytic solution of the present invention may comprise one or more components in addition to the above-described essential components (a nonaqueous solvent, a quaternary ammonium salt represented by the general formula (I), and an alkali metal cation) as long as the advantageous effects of the invention are achieved.

An electric double layer capacitor comprising the nonaqueous electrolytic solution as an electrolytic solution is also encompassed in the present invention. The electric double layer capacitor of the present invention can be any electric double layer capacitor that comprises the nonaqueous electrolytic solution as the electrolytic solution, and the production method therefor and the like are not particularly limited. The electric double layer capacitor of the present invention comprising the nonaqueous electrolytic solution is a highly durable electric double layer capacitor that is less prone to capacity decrease (capacity deterioration) and resistance increase.

EXAMPLES

The present invention will be described in further detail with reference to Examples below, but the invention is not limited to these Examples.

The concentrations of the alkali metal cations in each electrolytic solution and properties the electric double layer capacitors produced using the electrolytic solutions were determined by the following methods.

Method for quantitative determination of alkali metal cations Quantitative determination of potassium ions:

Measurement was carried out by ion chromatography.
Column: Dionex Ion Pac CS14, Ø4×250 mm (Nippon Dionex)
Detection method: electric conductivity
Suppressor: CSRS300 (product name, Nippon Dionex)
Suppressor current value: 35 mA
Mobile phase: 0.010 M methanesulfonic acid solution
Regeneration solution: ultrapure water (2 mL/min)
Mobile phase flow rate: 1.0 mL/min
Column temperature: 30° C.
Cell temperature: 35° C.
Sample injection volume: 25 µL
Measurement method: The reference standard (0.1 ppm potassium solution) and the sample solutions (about 500 mg of a sample was diluted with ultrapure water to give a 50-mL solution) were analyzed. From the obtained peaks, the concentrations were calculated in accordance with the following calculation expression.

Potassium ion ($K^+$) concentration (ppm)=peak area of $K^+$ in sample solution×0.1×50/sample amount (mg)/peak area of $K^+$ in standard solution×1,000

In each of the analyses of $Na^+$ and other alkali metal cations, an appropriate reference standard was used instead of the potassium solution.

Evaluation of properties of electric double layer capacitor:

Method for Producing Capacitor

A device (3 cm×5 cm: 5 pieces were stacked) was produced using the materials shown below and was subjected to vacuum drying at 180° C. for 15 hours. The device was then impregnated with an electrolytic solution (electrolytic solution amount: 0.097 cc/F), yielding a laminate cell (electric double layer capacitor). The produced electric double layer capacitor was subjected to aging treatment for 24 hours while a voltage of 2.7 V was applied to the capacitor at room temperature, and the initial properties were determined.

Electrode: a sheet electrode purchased from Japan Gore-Tex
Electrolytic paper (separator): TF4050 manufactured by Nippon Kodoshi
Electrolytic solution: the electrolytic solutions prepared in Examples 1 to 5 and Comparative Examples 1 to 4

The initial capacity and the internal resistance of the electric double layer capacitor were determined with an applied voltage of 2.7 v. After storage at 60° C. tor 2,000 hours with an applied voltage of 2.7 V, the capacity was determined, and the capacity deterioration rate relative to the initial capacity was calculated. The internal resistance was determined by an alternating-current two-terminal method at a frequency of 1 kHz.

The method for preparing electrolytic solutions used in Examples and Comparative Examples was as described below. The propylene carbonate used in Examples and Comparative Examples was a superfractionated, highly pure propylene carbonate (purity: 99.99%).

Production Example 1

According to the method described in the example 1 of JP 08-31401 B, N-ethyl-N-methyl pyrrolidinium tetrafluoroborate was produced.

Production Example 2

In an aqueous solution containing 0.5 mg of $NaBF_4$ and 20 mg of $KBF_4$, 1000 g of the N-ethyl-N-methyl pyrrolidinium tetrafluoroborate produced in Production Example 1 was dissolved. The solution was concentrated under reduced pressure until slurried, and then the pressure was returned to ordinary pressure. The slurry was recrystallized by addition of 2000 g of isopropanol to give N-ethyl-N-methyl pyrrolidinium tetrafluoroborate as white crystals.

Production Example 3

The same procedure was performed as in Production Example 2 except that 20 mg of $NaBF_4$ and 0.3 mg of $KBF_4$ were used instead of 0.5 mg of $NaBF_4$ and 20 mg of $KBF_4$ to give N-ethyl-N-methyl pyrrolidinium tetrafluoroborate as white crystals.

Production Example 4

According to the method described in the example 1 of JP 08-31401 B except that N,N,N-trimethyl ammonium bromide was used instead of 1-ethyl-1-methyl pyrrolidinium bromide, N,N,N-triethyl-N-methyl ammonium tetrafluoroborate was produced.

Production Example 5

The same procedure was performed as in Production Example 2 except that N,N-triethyl-N-methyl ammonium tetrafluoroborate produced in Production Example 4 was used instead of N-ethyl-N-methyl pyrrolidinium tetrafluoroborate to give N,N,N-triethyl-N-methyl ammonium tetrafluoroborate as white crystals.

Production Example 6

The same procedure was performed as in Production Example 3 except that N,N,N-triethyl-N-methyl ammonium tetrafluoroborate produced in Production Example 4 was used instead of N-ethyl-N-methyl pyrrolidinium tetrafluoroborate to give N,N,N-triethyl-N-methyl ammonium tetrafluoroborate as white crystals.

Comparative Example 1

An electrolytic solution was prepared by dissolving, at room temperature, in a dry nitrogen atmosphere with a dew point of −40° C., N-ethyl-N-methyl pyrrolidinium tetrafluoroborate produced in Production Example 1 as the electrolyte at a concentration of 1.5 mol/L in a highly pure propylene carbonate, Table 1 shows the properties of the electric double layer capacitor produced using the electrolytic solution.

Comparative Example 2

An electrolytic solution was prepared by dissolving, at room temperature, in a dry nitrogen atmosphere with a dew point of −40° C., N-ethyl-N-methyl pyrrolidinium tetrafluoroborate produced in Production Example 2 as the electrolyte at a concentration of 1.5 mol/L in a highly pure propylene carbonate. Table 1 shows the properties of the electric double layer capacitor produced using the electrolytic solution.

Example 1

To 100 g of dichloromethane, 100 g of N-ethyl-N-methyl pyrrolidinium tetrafluoroborate produced in Production Example 2 was added and dissolved at 25° C., and the solution was filtered through a 0.45-μm membrane filter. The filtrate was concentrated, recrystallized by addition of isopropanol, and cooled to 5° C. The crystals were collected by filtration, washed with isopropanol at 5° C., and then dried under reduced pressure. Except for using the crystals obtained in this way, the same method as in Comparative Example 1 was performed to give an electrolytic solution. Table 1 shows the properties of the electric double layer capacitor produced using the electrolytic solution.

Example 2

To 100 g of dichloromethane, 100 g of N-ethyl-N-methyl pyrrolidinium tetrafluoroborate produced in Production Example 2 was added and dissolved at 5° C., and the solution was filtered through a 0.45 μm membrane filter. The filtrate was concentrated, recrystallized by addition of isopropanol, and cooled to 5° C. The crystals were collected by filtration, washed with isopropanol at 5° C., and then dried under reduced pressure. Except for using the crystals obtained in this way as the electrolyte, the same method as in Comparative Example 1 was performed to give an electrolytic solution. Table 1 shows the properties of the electric double layer capacitor produced using the electrolytic solution.

Comparative Example 3

An electrolytic solution was prepared by dissolving, at room temperature, in a dry nitrogen atmosphere with a dew point of 40° C., N-ethyl-N-methyl pyrrolidinium tetrafluoroborate produced in Production Example 3 as the electrolyte at a concentration of 1.5 mol/L in a highly pure propylene carbonate. Table 1 shows the properties of the electric double layer capacitor produced using the electrolytic solution.

Example 3

To 100 g of dichloromethane, 100 g of the same N-ethyl-N-methyl pyrrolidinium tetrafluoroborate as that used in Production Example 3 was added and dissolved at 5° C., and the solution was filtered through a 0.45-μm membrane filter. The filtrate was concentrated, recrystallized by addition of isopropanol, and cooled to 5° C. The crystals were collected by filtration, washed with isopropanol at 5° C., and then dried under reduced pressure. Except for using the crystals obtained in this way as the electrolyte, the same method as in Comparative Example 2 was performed to give an electrolytic solution. Table 1 shows the properties of the electric double layer capacitor produced using the electrolytic solution.

Comparative Example 4

An electrolytic solution was prepared by dissolving, at room temperature, in a dry nitrogen atmosphere with a dew point of −40° C., N,N,N-triethyl-N-methyl ammonium tetrafluoroborate produced in Production Example 5 as the electrolyte at a concentration of 1.5 mol/L in a highly pure propylene carbonate. Table 1 shows the properties of the electric double layer capacitor produced using the electrolytic solution.

Example 4

To 100 g of dichloromethane, 100 g of N,N,N-triethyl-N-methyl ammonium tetrafluoroborate produced in Production Example 5 was added and dissolved at 5° C., and the solution was filtered through a 0.45-μm membrane filter. The filtrate was concentrated, recrystallized by addition of isopropanol, and cooled to 5° C. The crystals were collected by filtration, washed with isopropanol at 5° C., and then dried under reduced pressure. Except for using the crystals obtained in this way as the electrolyte, the same method as in Comparative Example 4 was performed to give an electrolytic solution. Table 1 shows the properties of the electric double layer capacitor produced using the electrolytic solution.

Example 5

To 100 g of dichloromethane, 100 g of N,N,N-triethyl-N-methyl ammonium tetrafluoroborate produced in Production Example 6 was added and dissolved at 5° C., and the solution was filtered through a 0.45-μm membrane filter. The filtrate was concentrated, recrystallized by addition of isopropanol, and cooled to 5° C. The crystals were collected by filtration, washed with isopropanol at 5° C., and then dried under reduced pressure. Except for using the crystals obtained in this way as the electrolyte, the same method as in Comparative Example 5 was performed to give an electrolytic solution. Table 1 shows the properties of the electric double layer capacitor produced using the electrolytic solution.

TABLE 1

Initial capacity and capacity change rate of capacitors produced using different electrolytic solutions

|  | Electrolytic solution | $K^+$ concentration | $Na^+$ concentration | Properties of electric double layer capacitor | |
|---|---|---|---|---|---|
|  |  |  |  | Initial capacity | Capacity deterioration rate |
| Example 1 | N-ethyl-N-methyl pyrrolidinium tetrafluoroborate/PC | 28.3 ppm | 0.4 ppm | 18.2 F | −9.0% |
| Example 2 | N-ethyl-N-methyl pyrrolidinium tetrafluoroborate/PC | 13.5 ppm | 0.3 ppm | 18.1 F | −8.7% |
| Comparative Example 1 | N-ethyl-N-methyl pyrrolidinium tetrafluoroborate/PC | N.D. | N.D. | 18.1 F | −14.3% |
| Comparative Example 2 | N-ethyl-N-methyl pyrrolidinium tetrafluoroborate/PC | 48.0 ppm | 0.3 ppm | 18.1 F | −15.0% |
| Example 3 | N-ethyl-N-methyl pyrrolidinium tetrafluoroborate/PC | 0.2 ppm | 12.7 ppm | 18.2 F | −9.3% |
| Comparative Example 3 | N-ethyl-N-methyl pyrrolidinium tetrafluoroborate/PC | 0.4 ppm | 45.0 ppm | 18.1 F | −14.8% |
| Example 4 | N,N,N-triethyl-N-methyl ammonium tetrafluoroborate/PC | 11.0 ppm | 0.3 ppm | 17.5 F | −15.3% |
| Comparative Example 4 | N,N,N-triethyl-N-methyl ammonium tetrafluoroborate/PC | 45.0 ppm | 0.3 ppm | 17.8 F | −17.8% |
| Example 5 | N,N,N-triethyl-N-methyl ammonium tetrafluoroborate/PC | 0.6 ppm | 2.5 ppm | 17.4 F | −15.1% |
| Comparative Example 5 | N,N,N-triethyl-N-methyl ammonium tetrafluoroborate/PC | 0.7 ppm | 42.0 ppm | 17.7 F | −18.0% |

Comparative Example 5

An electrolytic solution was prepared by dissolving, at room temperature, in a dry nitrogen atmosphere with a dew point of −40° C., N-triethyl-N-methyl ammonium tetrafluoroborate produced in Production Example 6 as the electrolyte at a concentration of 1.5 mol/L in a highly pure

The invention claimed is:
1. A nonaqueous electrolytic solution for electric double layer capacitors prepared by dissolving a quaternary ammonium salt represented by formula (I):

$$Q^+X^- \qquad (I),$$

wherein $Q^+$ represents a quaternary ammonium cation comprising pyrrolidinium, and $X^-$ represents a counter ion selected from the group consisting of $PF_6^-$, $BF_4^-$,  $AsF_6^-$, $N(CF_3SO_3)_2^-$, $SbF_6^-$, and $RfSO_3^-$, wherein Rf is a fluoroalkyl group having 1 to 8 carbon atoms, as an electrolyte in a nonaqueous solvent, wherein:

the quaternary ammonium salt excludes spiro quaternary ammonium tetrafluoroborate, the nonaqueous solvent is at least one solvent selected from the group consisting of propylene carbonate, ethylene carbonate, butylene carbonate, sulfolane, methylsulfolane, dimethyl carbonate, ethyl methyl carbonate, diethyl carbonate, γ-butyrolactone and mixtures thereof, and an alkali metal cation concentration is more than 10 ppm and not more than 30 ppm.

2. The nonaqueous electrolytic solution according to claim 1, wherein the alkali metal cation concentration is 12 to 30 ppm.

3. The nonaqueous electrolytic solution according to claim 1, wherein the alkali metal cation is a sodium ion and/or a potassium ion.

4. The nonaqueous electrolytic solution according to claim 1, wherein the quaternary ammonium cation is N-ethyl-N-methyl pyrrolidinium.

5. The nonaqueous electrolytic solution according to claim 1, wherein the $X^-$ in the formula (I) is $BF_4^-$.

6. An electric double layer capacitor comprising the nonaqueous electrolytic solution according to claim 1 as an electrolytic solution.

* * * * *